United States Patent
Shi et al.

(10) Patent No.: US 10,201,175 B2
(45) Date of Patent: Feb. 12, 2019

(54) N-ACYLATED 1-AMINOCYCLOALKYL CARBOXYLIC ACIDS AS FOOD FLAVOURING COMPOUNDS

(71) Applicant: Givaudan S.A., Vernier (CH)

(72) Inventors: Feng Shi, Mason, OH (US); Harry Renes, Almere (NL); Esther Van Ommeren, Almere (NL); Susanna Magdalena Vorster, Bussum (NL); Yili Wang, Mason, OH (US); Adri De Klerk, Made (NL); Stephan Haiber, Almere (NL); Eric Houben, Almere (NL); Jacob Elings, Huizen (NL)

(73) Assignee: GIVAUDAN SA, Vernier (CH)

(*) Notice: Subject to any disclaimer, the term of this patent is extended or adjusted under 35 U.S.C. 154(b) by 123 days.

(21) Appl. No.: 14/386,084

(22) PCT Filed: Mar. 28, 2013

(86) PCT No.: PCT/US2013/034342
§ 371 (c)(1),
(2) Date: Sep. 18, 2014

(87) PCT Pub. No.: WO2013/148997
PCT Pub. Date: Oct. 3, 2013

(65) Prior Publication Data
US 2015/0044347 A1    Feb. 12, 2015

Related U.S. Application Data

(60) Provisional application No. 61/617,796, filed on Mar. 30, 2012.

(51) Int. Cl.
| | | |
|---|---|---|
| A23F 5/24 | (2006.01) |
| A23L 2/56 | (2006.01) |
| C12C 5/02 | (2006.01) |
| C12G 3/06 | (2006.01) |
| A23C 19/09 | (2006.01) |
| A23C 20/02 | (2006.01) |
| A23L 11/00 | (2016.01) |
| A23L 19/18 | (2016.01) |
| A23L 19/20 | (2016.01) |
| A23L 23/10 | (2016.01) |
| A23L 27/20 | (2016.01) |
| A23L 27/21 | (2016.01) |
| A23L 27/50 | (2016.01) |
| A23L 27/60 | (2016.01) |
| A23L 7/161 | (2016.01) |
| C07C 233/52 | (2006.01) |

(52) U.S. Cl.
CPC .......... *A23L 7/161* (2016.08); *A23C 19/0904* (2013.01); *A23C 19/0925* (2013.01); *A23C 20/025* (2013.01); *A23F 5/243* (2013.01); *A23L 2/56* (2013.01); *A23L 11/09* (2016.08); *A23L 19/18* (2016.08); *A23L 19/20* (2016.08); *A23L 23/10* (2016.08); *A23L 27/203* (2016.08); *A23L 27/21* (2016.08); *A23L 27/50* (2016.08); *A23L 27/60* (2016.08); *C07C 233/52* (2013.01); *C12C 5/026* (2013.01); *C12G 3/06* (2013.01); *A23V 2002/00* (2013.01); *C07C 2601/02* (2017.05); *C12G 2200/21* (2013.01)

(58) Field of Classification Search
CPC . A23L 7/161; A23L 2/56; A23L 11/09; A23L 19/18; A23L 19/20; A23L 27/203; A23L 27/21; A23L 27/50; A23L 27/60; A23L 23/10; A23F 5/243; C07C 233/52; C07C 2601/02; A23C 19/0904; A23C 19/0925; A23C 20/025; C12G 3/06; C12G 2200/21; C12C 5/026; A23V 2002/00
USPC .................... 426/534, 536, 538, 650
See application file for complete search history.

(56) References Cited

U.S. PATENT DOCUMENTS

| | | | |
|---|---|---|---|
| 2,835,590 A | 5/1958 | Rusoff et al. |
| 3,024,272 A | 3/1962 | Hyson et al. |
| 3,624,114 A | 11/1971 | Morelle |
| 3,801,633 A | 4/1974 | Toyoshima et al. |
| 3,878,305 A | 4/1975 | Damico et al. |

(Continued)

FOREIGN PATENT DOCUMENTS

| | | |
|---|---|---|
| AU | 675778 | 2/1997 |
| CN | 101597239 A | 12/2009 |

(Continued)

OTHER PUBLICATIONS

International Search for PCT/US2013/034342 dated Jul. 12, 2013.
Written Opinion of the International Searching Authority for PCT/US2013/034342 dated Jul. 12, 2013.
Burstein, et al., "Potential anti-Inflammatory actions of elmiric (lipoamino)acids", Bioorganic & Medical Chemistry, Pergamon, GB, vol. 15, No. 10, Apr. 7, 2007, pp. 3345-3355.

(Continued)

*Primary Examiner* — Leslie A Wong
(74) *Attorney, Agent, or Firm* — Norris McLaughlin PA

(57) ABSTRACT

Compounds represented by the formula

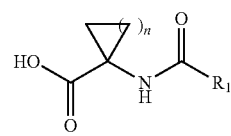

and their edible salts, and edible compositions containing same
wherein
R₁ is an alkyl residue containing 6 to 20 carbon atoms, or an alkene residue containing from 9 to 25 carbon atoms with 1 to 6 double bonds, such that R₁ together with the carbonyl group to which it is attached is a residue of a carboxylic acid, and the amino acid residue connected to (Continued)

the carbonyl carbon atom is a residue of a 1-amino cycloalkane carboxylic acid (ACCA),
and n is 1, 2, 3 or 4.

22 Claims, No Drawings

(56) References Cited

U.S. PATENT DOCUMENTS

| | | |
|---|---|---|
| 3,940,500 A | 2/1976 | Sortwell, III |
| 3,947,589 A | 3/1976 | Misato et al. |
| 4,016,287 A | 4/1977 | Eberhardt et al. |
| 4,066,799 A | 1/1978 | Cornelius et al. |
| 4,093,740 A | 6/1978 | Fahnenstich et al. |
| 4,248,859 A | 2/1981 | Roswell et al. |
| 4,442,090 A | 4/1984 | Kakeya et al. |
| 4,448,785 A | 5/1984 | Kathawala et al. |
| 4,479,974 A | 10/1984 | Schenz |
| 4,757,066 A | 7/1988 | Shiokari et al. |
| 4,777,195 A | 10/1988 | Hesse et al. |
| 5,164,414 A | 11/1992 | Vincent et al. |
| 5,176,934 A | 1/1993 | Lee |
| 5,286,480 A | 2/1994 | Boggs et al. |
| 5,312,831 A | 5/1994 | Ayral-Kaloustian et al. |
| 5,780,090 A | 7/1998 | Firmenich |
| 6,251,931 B1 | 6/2001 | Boger et al. |
| 7,320,807 B2 | 1/2008 | Asher et al. |
| 7,981,457 B2 | 7/2011 | Visser et al. |
| 8,778,437 B2 | 7/2014 | Renes et al. |
| 8,828,469 B2 | 9/2014 | Langer et al. |
| 8,945,651 B2 | 2/2015 | Visser et al. |
| 9,560,846 B2 | 2/2017 | Riera et al. |
| 9,560,876 B2 | 2/2017 | Riera et al. |
| 2001/0002257 A1 | 5/2001 | Stolz |
| 2001/0014695 A1 | 8/2001 | Behl et al. |
| 2004/0081708 A1 | 4/2004 | Baxter |
| 2004/0157932 A1 | 8/2004 | Saebo |
| 2005/0031789 A1 | 2/2005 | Liu et al. |
| 2007/0282002 A1 | 12/2007 | Maezono et al. |
| 2008/0038428 A1 | 2/2008 | Visser et al. |
| 2008/0038429 A1 | 2/2008 | Visser et al. |
| 2008/0038430 A1 | 2/2008 | Visser et al. |
| 2008/0050500 A1 | 2/2008 | Muranishi et al. |
| 2009/0057618 A1 | 3/2009 | Leinweber et al. |
| 2011/0081473 A1 | 4/2011 | Hamasaki et al. |
| 2013/0022728 A1 | 1/2013 | Popplewell et al. |
| 2015/0044332 A1 | 2/2015 | Shi et al. |
| 2015/0044347 A1 | 2/2015 | Shi et al. |
| 2015/0050408 A1 | 2/2015 | Shi et al. |
| 2015/0064326 A1 | 3/2015 | Shi et al. |
| 2015/0064327 A1 | 3/2015 | Shi et al. |
| 2015/0072060 A1 | 3/2015 | Shi et al. |
| 2015/0086694 A1 | 3/2015 | Shi et al. |

FOREIGN PATENT DOCUMENTS

| | | |
|---|---|---|
| CN | 102028176 A | 4/2011 |
| CN | 102036571 B | 7/2013 |
| DE | 2234399 | 1/1974 |
| EP | 0030448 B1 | 4/1985 |
| EP | 0198348 A2 | 10/1986 |
| EP | 0208279 A1 | 1/1987 |
| EP | 0271816 A2 | 12/1987 |
| EP | 0356784 A2 | 3/1990 |
| EP | 0432039 A2 | 6/1991 |
| EP | 0443891 A1 | 8/1991 |
| EP | 0460566 A2 | 12/1991 |
| EP | 0500332 A2 | 8/1992 |
| EP | 0891764 A1 | 1/1999 |
| EP | 1263286 | 12/2002 |
| EP | 1356744 A1 | 10/2003 |
| EP | 1471052 A1 | 10/2004 |
| EP | 1520850 A2 | 4/2005 |
| EP | 1637042 A1 | 3/2006 |
| EP | 2031092 A2 | 3/2009 |
| EP | 2058297 A1 | 5/2009 |
| EP | 2119373 A1 | 11/2009 |
| EP | 2140770 A1 | 1/2010 |
| EP | 2184051 A1 | 5/2010 |
| EP | 2382871 A1 | 11/2011 |
| EP | 2597082 A1 | 5/2013 |
| FR | 1603799 A | 5/1971 |
| FR | 2765109 A1 | 12/1998 |
| FR | 2878439 A1 | 6/2006 |
| GB | 1130480 | 10/1968 |
| GB | 1130480 A | 10/1968 |
| GB | 1426545 | 9/1973 |
| GB | 1377271 | 12/1974 |
| GB | 1436614 | 5/1976 |
| GB | 1560000 | 1/1980 |
| GB | 2200633 A | 8/1988 |
| JP | S4614357 Y1 | 5/1971 |
| JP | S4985244 A | 8/1974 |
| JP | S49124244 | 11/1974 |
| JP | 52-94453 A | 8/1977 |
| JP | S53118516 A | 10/1978 |
| JP | 5690046 A | 7/1981 |
| JP | S56123910 A | 9/1981 |
| JP | S56131365 A | 10/1981 |
| JP | S63156849 A | 6/1988 |
| JP | S63218649 A | 9/1988 |
| JP | H2256608 A | 10/1990 |
| JP | H06157440 A | 6/1994 |
| JP | H08103242 A | 4/1996 |
| JP | H08103242 A1 | 4/1996 |
| JP | H08208453 A | 8/1996 |
| JP | 9313129 A | 12/1997 |
| JP | 2824158 B2 | 11/1998 |
| JP | 2006296356 A | 11/2006 |
| JP | 201229616 A | 2/2012 |
| RU | 2335926 C1 | 10/2008 |
| WO | 8603944 A1 | 7/1986 |
| WO | 8701935 A1 | 4/1987 |
| WO | 9738688 A1 | 10/1997 |
| WO | 0057726 A1 | 10/2000 |
| WO | 01030143 A2 | 5/2001 |
| WO | 0159067 A2 | 8/2001 |
| WO | 01569067 A2 | 8/2001 |
| WO | 02094764 A1 | 11/2002 |
| WO | 0334842 A1 | 5/2003 |
| WO | 2004000787 A2 | 12/2003 |
| WO | 2004075663 A1 | 9/2004 |
| WO | 2005096843 A1 | 10/2005 |
| WO | 2005096844 A1 | 10/2005 |
| WO | 2005102071 A1 | 11/2005 |
| WO | 2006009425 A1 | 1/2006 |
| WO | 2006010590 A1 | 2/2006 |
| WO | 2006046853 A1 | 5/2006 |
| WO | 2008040756 A1 | 4/2008 |
| WO | 2009021558 A1 | 2/2009 |
| WO | 2009141294 A1 | 11/2009 |
| WO | 2010022914 A1 | 3/2010 |
| WO | 2011141685 A2 | 5/2011 |
| WO | 2011105985 A1 | 9/2011 |
| WO | 2011141685 A2 | 11/2011 |
| WO | 2012071293 A2 | 5/2012 |
| WO | 2013010991 A1 | 1/2013 |
| WO | 2013148991 A1 | 10/2013 |
| WO | 2013148997 A1 | 10/2013 |
| WO | 2013149008 A2 | 10/2013 |
| WO | 2013149012 A1 | 10/2013 |
| WO | 2013149019 A1 | 10/2013 |
| WO | 2013149022 A1 | 10/2013 |
| WO | 2013149025 A1 | 10/2013 |
| WO | 2013149031 A2 | 10/2013 |
| WO | 2013149035 A2 | 10/2013 |

OTHER PUBLICATIONS

International Search Report for corresponding application PCT/EP2013/070534 dated Aug. 11, 2014.

(56) References Cited

OTHER PUBLICATIONS

Written Opinion of the International Searching Authority for corresponding application PCT/EP2013/070534 dated Aug. 11, 2014.
International Search Report for corresponding application PCT/EP2013/070540 dated Nov. 10, 2014.
International Search Report for corresponding application PCT/EP2014/071021 dated Oct. 12, 2014.
Written Opinion of the International Searching Authority for corresponding application PCT/EP2014/071021 dated Oct. 12, 2014.
International Search Report for corresponding application PCT/EP2014/071056 dated Dec. 12, 2014.
International Search Report for corresponding application PCT/US2013/034299 dated Sep. 27, 2013.
Written Opinion of the International Searching Authority for corresponding application PCT/US2013/034299 dated Sep. 27, 2013.
International Search Report for corresponding application PCT/US2013/034335 dated Jul. 12, 2013.
Written Opinion of the International Searching Authority for corresponding application PCT/US2013/034335 dated Jul. 12, 2013.
International Search Report for corresponding application PCT/US2013/034375 dated Jul. 15, 2013.
Written Opinion of the International Searching Authority for corresponding application PCT/US2013/034375 dated Jul. 15, 2013.
International Preliminary Report on Patentability for corresponding application PCT/US2013/034375 dated Oct. 1, 2014.
International Search Report for corresponding application PCT/US2013/034388 dated Jul. 19, 2013.
Written Opinion of the International Searching Authority for corresponding application PCT/US2013/034388 dated Jul. 19, 2013.
International Preliminary Report on Patentability for corresponding application PCT/US2013/034388 dated Oct. 1, 2014.
International Search Report for corresponding application PCT/US2013/062966 dated Sep. 17, 2014.
International Search Report for corresponding application PCT/US2013/062993 dated Jun. 5, 2014.
International Search Report for corresponding application PCT/US2013/063008 dated Aug. 19, 2014.
International Search Report for corresponding application PCT/US2013/063014 Aug. 6, 2014.
International Search Report for corresponding application PCT/US2013/034355 dated Oct. 7, 2013.
Written Opinion of the International Searching Authority for corresponding application PCT/US2013/034355 dated Oct. 7, 2013.
International Preliminary Report on Patentability for corresponding application PCT/US2013/034355 dated Oct. 1, 2014.
Written Opinion of the International Searching Authority for corresponding application PCT/US2013/034363 dated Jul. 18, 2013.
International Preliminary Report on Patentability for corresponding application PCT/US2013/0343563 dated Oct. 1, 2014.
International Search Report for corresponding application PCT/US2013/034363 dated Jul. 18, 2013.
International Search Report for corresponding application PCT/US2013/034378 dated Jul. 12, 2013.
Written Opinion of the International Searching Authority for corresponding application PCT/US2013/034378 dated Jul. 12, 2013.
International Preliminary Report on Patentability for corresponding application PCT/US2013/034378 dated Oct. 1, 2014.
International Search Report for corresponding application PCT/US2013/034395 dated Nov. 18, 2013.
Written Opinion of the International Searching Authority for corresponding application PCT/US2013/034395 dated Nov. 18, 2013.
International Preliminary Report on Patentability for corresponding application PCT/US2013/034395 dated Oct. 1, 2014.
International Search Report for corresponding application PCT/US2013/034403 dated Nov. 6, 2013.
Written Opinion of the International Searching Authority for corresponding application PCT/US2013/034403 dated Nov. 6, 2013.
International Preliminary Report on Patentability for corresponding application PCT/US2013/034403 dated Oct. 1, 2014.

T. Amagata, et al. "Gymnastatins F-H, Cytostatic Metabolites from the Sponge-Derived Fungus Gymnascella dankaliensis", American Chemical Society and American Society of Pharmacognosy, vol. 69, pp. 1384-1388, 2006.
"Aromat", Wikipedia, the free encyclopedia, http://en.wikipedia.org/wiki/Aromat.
S. H. Burstein, et al., "Potential anti-inflammatory actions of the elmiric (lipoamino) acids", Bioorganic & Medicinal Chemistry, vol. 15, pp. 3345-3355, 2007.
G.M. Dumowchik, et al., "The In vitro effects of Three Lysosomotropic Detergents Against Three Human Tumor Cell Lines", Bioorganic & Medicinal Chemisty Letters, vol. 5, No. 8, pp. 893-898, 1995, Great Britain.
M. Fieser, et al., "Synthetic Emulsify Agents", Chemical Laboratory of Harvord University, pp. 2825-2832, Jun. 20, 1956.
S. N. Georgiades, et al., "Synthetic libraries of tyrosine-derived bacterial metabolites", Bioorganic & Medicinal Chemisty Letters, vol. 18, pp. 3117-3121, 2008.
N. Gregersen, et al., "Gas Chromatographic Mass Spectrometric Identification of N-Dicarboxylmonoglycines", Biomedical Mass Spectrometry, vol. 5, No. 1, pp. 80-83, 1978.
L. Guan, et al. "Synthesis and Anticonvulsant Activity of N-(2-Hydroxy-ethyl)amide Derivatives", Arch. Pharm. Chem. Life Sci. vol. 342, pp. 24-40, 2009.
V. Gududuru, et al., "Synthesis and biological evaluation of novel cytotoxic phospholipids for prostate cancer", Bioorganic & Medicinal Chemisty Letters, vol. 14, pp. 4919-4923, 2004.
C. Leschke, et al., "Alkyl-Substituted Amino Acid Amides and Analogous Di- and Triamines: New Non-Peptide G Protein Activators", Journal of Medicinal Chemistry, vol. 40, pp. 3130-3139, 1997.
A. Leydet, et al., "Polyanion Inhibitors of Human Immunodeficiency Virus and other Viruses, Part 2. Polymerized Anionic Surfactants Derived from Amino Acids and Dipeptides", Journal of Medicinal Chemistry, vol. 39, No. 8, pp. 1626-1634, 1996.
R. H. Mazur, et al., "Structure-Taste Relationships of Aspartic Acid Amides", Journal of Medicinal Chemistry, vol. 13, No. 6, pp. 1217-1221, 1970.
R. C. McKellar, et al., "Antimicrobial activity of fatty N-acylamino acids against Gram-positive foodborne pathogens", Food Microbiology, vol. 9, pp. 67-76, 1992.
C. Menozzi-Smarrito, et al., "Synthesis and Evaluation of New Alkylamides Derived from a-Hydroxysanshool, the Pungent Molecule in Szechuan Pepper", Journal of Agricultural and Food Chemistry, vol. 57, pp. 1982-1989, 2009.
A. Pal, et al., "Molecular mechanism of physical gelation of hydrocarbons by fatty acid amides of natural amino acids", Tetrahedron, vol. 63, pp. 7334-7348, 2007.
E. Piera, et al., "Qualitative and Quantitative analysis of new alkyl arginine surfactants by high-performance liquid chromatoghraphy and capillary electrophoresis", Journal of Chromatography A, vol. 852, pp. 499-506, 1999.
S. Y. Mhaskar, et al., "Synthesis of N-Acyl Amino Acids and Correlation of Structure with Surfactant Properties of Their Sodium Salts", JAOCS, vol. 67, No. 12, pp. 1015-1019, 1990.
C. L. Penney, et al., "Further studies on the adjuvanticity of stearyl tyrosine and amide analogues", Vaccine, vol. 12, No. 7, pp. 629-632, 1994.
C. W. Phoon, et al., "Isolation and total synthesis of gymnastatin N, a POLO-like kinase 1 active constituent from the fungus *Arachniotus punctatus*", Tetrahedron, vol. 60, pp. 11619-11628, 2004.
C. M. Ranger, et al.,"Mass spectral characterization of fatty acid amides from alfalfa trichomes and their deterrence against the potato leafhopper", Phytochemistry, vol. 66, pp. 529-541, 2005.
M. Schlitzer, et al., "Design, Synthesis and Early Structure-Activity Relationship of Farnesyltransferase Inhibitors Which Mimic Both the Peptidic and the Prenylic Substrate", Bioorganic & Medicinal Chemisty , vol. 8, pp. 1991-2006, 2000.
S. Tadashi, et al., "Aliphatic Acylamino Acids", Pharm. Society Japan, vol. 86, No. 10, pp. 967-972, 1966, Japan.
K. Takao, et al., "Studies on Inhibition of Enzymatic Arginyltransfer Reaction", Chem. Pharm. Bull. vol. 46, No. 7, pp. 1169-1172, 1998, Japan.

(56) References Cited

OTHER PUBLICATIONS

C. Toniolo, et al., "Effect of Na-acyl Chain Length on the Membrane-Modifying Properties of Synthetic Analogs of the Lipopeptaibol Trichogin GA IV", Journal of American Chemical Society, vol. 118, pp. 4952-4958, 1996.
K. Watanabe, et al., "Pharmacological Effects in Mice of Anandamide and Its Related Fatty Acid Ethanolamides, and Enhancement of Cataleptogenic Effect of Anandamide by Phenylmethylsulfonyl Fluoride", Bio. Pharm. Bull., vol. 22, No. 4, pp. 366-370, 1999.
A. Kolokouris, et al., "Studies on Pyrrolidinones, Synthesis of some N-Fatty Acylpyroglutamic Acids", J. Heterocyclic Chem., vol. 32, pp. 1489-1492, 1995.
M. Saito, et al., "Sythesis and Inhibitory Activity of Acyl-Peptidyl-Pyrrolidine Derivatives Toward Post-Proline Cleaving Enzyme; A Study of Subsite Specificity", Journal of Enzyme Inhibition, vol. 5, pp. 51-75, 1991, United Kingdom.
J. P. Ley, "Masking Bitter Taste by Molecules", Chemical Perception, 2008, vol. 1, pp. 58-77.
C. Ma, et al., "Effect of Fatty N-Acylamino Acids on Some Functional Properties of Two Food Proteins", J. AgrigFood Chem, 1993, vol. 41, pp. 1182-1188.
A. Paquet, "Preparation of some long-chain N-acyl derivatives of essential amino acids for nutritional studies", Canada Journal Biochem., vol. 58, National Research Council of Canada, pp. 573-576, 1980.
M. Gerova, et al., "Self-assembly properties of some chiral N-Palmitoyl amino acid surfactants in aqueous solution", ScienceDirect, Journal of Colloid and Interface Science, 2008, vol. 319, pp. 526-533.
R. Damico, "An Investigation of N-Substituted Methionine Derivatives for Food Supplementation", J. Agr. Food Chem., vol. 23, No. 1, pp. 30-33, 1975.
English translation of first Japanese Office Action for corresponding application JP 2015-503564 dated Dec. 15, 2016.
Written Opinion of the Intellectual Property Office of Singapore for corresponding application CN 11201405104P dated May 30, 2016.
English translation of second Chinese Office Action for corresponding application CN 201380017898.7 dated May 3, 2016.
English translation of first Japanese Office Action for corresponding application JP 2015-503572 dated Dec. 15, 2016.
English translation of second Chinese Office Action for corresponding application CN 201380017847.4 dated May 5, 2016.
English translation of third Chinese Office Action for corresponding application CN 201380017847.4 dated Nov. 22, 2016.
English translation of first Japanese Office Action for corresponding application JP 2015-503573 dated Dec. 14, 2016.
English translation of second Chinese Office Action for corresponding application CN 201380017924.6 dated May 31, 2016.
English translation of first Japanese Office Action for corresponding application JP 2015-503577 dated Jan. 4, 2017.
English translation of first Japanese Office Action for corresponding application JP 2015-503584 dated Jan. 27, 2017.
English translation of first Japanese Office Action for corresponding application JP 2015-503579 dated Oct. 14, 2016.
English translation of second Chinese Office Action for corresponding application CN 201380017825.8 dated May 31, 2016.
English translation of first Japanese Office Action for corresponding application CN 201380017814.x dated Apr. 1, 2016.
English translation of second Chinese Office Action for corresponding application CN 201380017832.8 dated Mar. 31, 2016.
English translation of second Chinese Office Action for corresponding application CN 201380017831.3 dated Mar. 2, 2016.
Written Opinion of the Intellectual Property Office of Singapore for corresponding application CN 11201405188X dated Sep. 13, 2016.
Written Opinion of the Intellectual Property Office of Singapore for corresponding application CN 11201405295W dated Apr. 15, 2016.
Written Opinion of the Intellectual Property Office of Singapore for corresponding application CN 11201405409P dated May 11, 2016.
Written Opinion of the Intellectual Property Office of Singapore for corresponding application CN 11201405340X dated Mar. 24, 2016.
Written Opinion of the Intellectual Property Office of Singapore for corresponding application CN 11201405342T dated Mar. 23, 2016.
Written Opinion of the Intellectual Property Office of Singapore for corresponding application CN 11201601652X dated Sep. 22, 2016.
Second International Search Report for corresponding application PCT/US2013/034355 dated Oct. 7, 2013.
Second International Search Report for corresponding application PCT/US2013/034299 dated Sep. 27, 2013.
Second International Search Report for corresponding application PCT/US2013/034342 dated Jul. 12, 2013.
International Preliminary Report on Patentability for corresponding application PCT/US2013/034342 dated Oct. 1, 2014.
Written Opinion of the International Searching Authority for corresponding application PCT/US2013/034342 dated Jul. 12, 2013.
Second International Search Report for corresponding application PCT/US2013/034395 dated Nov. 18, 2013.
Second International Search Report for corresponding application PCT/US2013/034403 dated Nov. 6, 2013.
B. Tan, et al., "Identification of endogenous acyl amino acids based on a targeted lipidomics approach", Journal of Lipid Research, vol. 51, pp. 112-119, 2010.
Written Opinion of the Intellectual Property Office of Singapore for corresponding application CN 11201405413S dated Jun. 24, 2016.
U.S. Appl. No. 14/386,048, filed Sep. 18, 2014.
U.S. Appl. No. 14/386,061, filed Sep. 18, 2014.
U.S. Appl. No. 14/386,090, filed Sep. 18, 2014.
U.S. Appl. No. 14/386,100, filed Sep. 18, 2014.
U.S. Appl. No. 14/386,112, filed Sep. 18, 2014.
U.S. Appl. No. 14/386,126, filed Sep. 18, 2014.
U.S. Appl. No. 14/916,815, filed Mar. 4, 2016.
U.S. Appl. No. 14/916,806, filed Mar. 4, 2016.
U.S. Appl. No. 14/916,785, filed Mar. 4, 2016.
U.S. Appl. No. 14/916,793, filed Mar. 4, 2016.
U.S. Appl. No. 14/916,782, filed Mar. 4, 2016.
U.S. Appl. No. 14/916,830, filed Mar. 4, 2016.
U.S. Appl. No. 14/916,846, filed Mar. 4, 2016.
U.S. Appl. No. 14/916,861, filed Mar. 4, 2016.
U.S. Appl. No. 14/870,598.
Hession, "N-Acetylglutamate and N-Acetylaspartate in Soybeans (*Glycine max* L.), Maize (*Zea maize* L.), and Other Foodstuffs", Journal of Agricultural and Food Chemistry, 2008, 56, pp. 9121-9126.
Cameron, "13 Foods with Natural Umami", Readers Digest, (first posted on internet Aug. 3, 2010; downloaded May 28, 2016,from the site: http://www.rd.com/food/recipes-cooking/13-foods-with-natural-umami/) at pp. 1-5.
Doving, et al, "Chemical Senses and Flavour", D. Reidel Publishing Company, vol. 1, No. 4, Oct. 1975, pp. 387-401, USA.
Stenner, "Umami—The Science, Ingredients, and Cooking with the 'Fifth-taste'", published Dec. 11, 2009, downloaded from site: http://www.tulsafood.com/uncategorized/umami-the-science-ingredients-cooking-with-the-fifth-taste, 9 pages.
Kazda, "Sliced Cucumber and Tomato Salad from Life's Ambrosia", copyright 2009, downloaded May 28, 2016 from site: http://www.lifesambrosia.com/print-recipe/?pid=2064.
Umami Information Center/Umami Rich Foods, downloaded May 28, 2016; screen shot from Wayback Machine, dated May 5, 2011; from the site: http://www.umamiinfo.com/2011/03/umami-rich-food-vegetables.php ; 3 pages.
Roudot-Algaron, "Flavor Constituents of Aqueous Fraction Extracted from Comte Chees by Liquid Carbon Dioxide", Journal of Food Science, vol. 58, No. 5, 1993, pp. 1005-1009.
Umami Information center Web Page/Overview, first posted on the internet on Apr. 30, 2011, as found on the Internet ArchivelWayback Machine at http://www.web.archive.org/web/2011 0430102741/ http://www.umamiinfo.com/umami-rich-food/.
Tortoriello, "Targeted Lipidomics in *Drosophila melanogaster* Identifies Novel 2-Monoacylglycerols and N-acyl Amides", vol. 8, Issue 000.7, pp. 1-10, Jul. 2013, www.plosone.org.
International Preliminary Report on Patentability for related application PCT/US2013/034363 dated Oct. 1, 2014.
Rigo, et al., "Studies on Pyrrolidinones. Synthesis of some N-Fatty Acylpyroglutamic Acids", J. Heterocyclic Chem., vol. 32, pp. 1489-1491, 1995, XP-002224102.

N-ACYLATED 1-AMINOCYCLOALKYL CARBOXYLIC ACIDS AS FOOD FLAVOURING COMPOUNDS

This is an application filed under 35 USC 371 of PCT/US2013/034342, which claims priority to US 61/617796 dated 30 Mar.2012

The invention is concerned with certain carboxylic acid-amino acid conjugates, flavour compositions containing said conjugates, and their use in edible compositions.

The invention is concerned with certain carboxylic acid-amino acid conjugates, flavour compositions containing said conjugates, and their use in edible compositions.

Many food flavour ingredients are known in the art that exert their own very pronounced flavour characteristics to a food product. Such ingredients may be of great value in niche areas for particular types of food categories, but can be incongruous, or even offensive, when employed in other food categories.

There is a need to provide broad spectrum flavour ingredients that act to complement or accentuate the taste and mouthfeel characteristics of the edible compositions into which they are incorporated.

The applicant has now found a group of compounds that may be employed flavour ingredients that complement or accentuate the taste and mouthfeel characteristics of edible compositions into which they are incorporated across a wide category of flavour applications.

The present invention provides in a first aspect compounds represented by the following formula

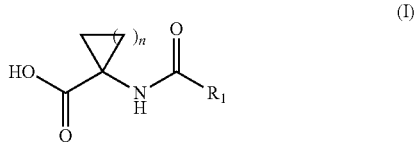

(I)

their edible salts, and their use in edible compositions wherein $R_1$ is an alkyl residue containing 6 to 20 carbon atoms, or an alkene residue containing from 9 to 25 carbon atoms with 1 to 6 double bonds, such that $R_1$ together with the carbonyl group to which it is attached is a residue of a carboxylic acid, and the amino acid residue connected to the carbonyl carbon atom is a residue of a 1-amino cycloalkane carboxylic acid (ACCA), and n is 1, 2, 3 or 4

Edible salts include those typically employed in the food and beverage industry and include chlorides, sulphates, phosphates, gluconates, sodium, citrates, carbonates, acetates and lactates.

The preferred compounds are those wherein "n" is 1.

The amino acid residue disclosed in the above formula may be abbreviated as "ACCA".

The carboxylic acids can likewise be represented in abbreviated form. The carboxylic acid residues may be referred to generally by the abbreviation Cn, wherein "n" represents the number of carbon atoms in the residue. For example, the residue of an 18 carbon acid may be abbreviated as C18. Still further, if the 18 carbon acid is saturated, e.g. stearic acid. It may be abbreviated as C18:0 (because it contains zero double bonds), whereas an 18 carbon acid having one double bond—e.g. oleic acid—may be abbreviated as C18:1. Still further, if the C18 acid has a single double bond in the cis configuration, then it can be abbreviated as C18:1c. Similarly, if the double bond was in the trans configuration, then the abbreviation becomes C18:1t.

In a particular embodiment of the present invention the carboxylic acid residue is a residue of a fatty acid.

The fatty acid residue may be the residue of a C8 to C22 fatty acid. The fatty acid may be mammalian or non-mammalian. A mammalian fatty acid is a natural or synthetic fatty acid that is identical in structure to one naturally produced in a mammal, including, but not limited to, myristic acid, palmitic acid, stearic acid, oleic acid, linoleic acid, linolenic acid, eicosatrienoic acid, arachidonic acid, eicosapentenoic acid, and docosatetraenoic acid. A non-mammalian fatty acid is a natural or synthetic fatty acid not normally produced by a mammal, including, but not limited to, pentadecanoic acid; heptadecanoic acid; nonadecanoic acid; heneicosanoic acid; 9-trans-tetradecenoic acid; 10-trans-pentadecenoic acid; 9-trans-hexadecenoic acid; 10-trans-heptadecenoic acid; 10-trans-heptadecenoic acid; 7-trans-nonadecenoic acid; 10,13-nonadecadienoic acid; 11-trans-eicosenoic acid; and 12-transhenicosenoic acid.

The fatty acid residues may be saturated or unsaturated. If they are unsaturated, it is preferred that they have 1, 2 or 3 double bonds, which may in cis- or trans-configuration. More particularly, the preferred fatty acid residues are C16 to C18, and may be saturated or unsaturated.

The skilled person will appreciate, however, that natural sources of these fatty acids, for example almond oil, avocado oil, castor oil, coconut oil, corn oil, cottonseed oil, olive oil, peanut oil, rice bran oil, safflower oil, sesame oil, soybean oil, sunflower oil, palm oil and canola oil, each consist of a complex mixture of fatty acids. For example, safflower oil is predominately a source of the C18:2 linoleic acid, nevertheless it may contain other fatty acids, such as linolenic acid (C18:3) and palmitic acid (C16:0), amongst others. Accordingly, reference herein to a compound containing a particular fatty acid residue, for example a residue of C18 fatty acid, may be a reference to a pure, or substantially pure C18 fatty acid residue, or it may relate to a mixture of fatty acid residues with the predominant residue being a C18 residue. Preferred fatty acid residues are C16 to C18.

It follows that the compounds of formula (I) can also be represented by this abbreviated form. For example, the compound of formula (I) consisting of a residue of a C18 carboxylic acid and a residue of the 1-amino cycloalkane carboxylic acid can be represented by the abbreviation C18-ACCA. For simplicity the compounds of formula (I) henceforth may be represented in this abbreviated form.

As is evident from the above formula (I), the amino nitrogen atom on the amino acid residue is bound to a carbonyl carbon atom of the carboxylic acid residue to form an amide linkage. Thus C18-ACCA represents the compound of formula (I) in which the residue of a 1-amino cycloalkane carboxylic acid is connected via its nitrogen atom to the carbonyl carbon atom of a C18 carboxylic acid.

The compounds include C8-ACCA, C9-ACCA, C10-ACCA, C12-ACCA, C14-ACCA, C16-ACCA, C18-ACCA, C20-ACCA and C22-ACCA.

The compounds include C8-ACCA, C9-ACCA, C10-ACCA, C12-ACCA, C14-ACCA, C16-ACCA, C18-ACCA, C20-ACCA and C22-ACCA, wherein the carboxylic acid residue is saturated.

The compounds include C8-ACCA, C9-ACCA, C10-ACCA, C12-ACCA, C14-ACCA, C16-ACCA, C18-ACCA, C20-ACCA and C22-ACCA, wherein the carboxylic acid residue is unsaturated and contains 1, 2 or 3 double bonds.

The double bonds may be in cis-configuration, trans-configuration or a mixture of cis- and trans-configuration.

The compounds include those specified above wherein the cycloalkane ring in the amino acid residue is cyclopropane (n=1).

Particularly preferred compounds are N-palmitoyl 1-amino-cyclopropyl carboxylic acid (C16:0-ACCA), N-stearoyl 1-amino-cyclopropyl carboxylic acid (C18:0-ACCA), N-linoleoyl 1-amino-cyclopropyl carboxylic acid (C18:2-ACCA), N-linolenoyl 1-amino-cyclopropyl carboxylic acid (C18:2-ACCA), N-oleoyl 1-amino-cyclopropyl carboxylic acid (C18:1-ACCA), N-(9-palmitenoyl) 1-amino-cyclopropyl carboxylic acid (C16:1-ACCA), N-decanoyl 1-amino-cyclopropyl carboxylic acid (C10:0-ACCA) and N-geranoyl 1-amino-cyclopropyl carboxylic acid (C10:2-ACCA).

The compounds of formula (I) can be formed by known methods using commercially available starting materials, reagents and solvents, and a detailed discussion is not warranted here. In an embodiment of the present invention, the conjugates can be formed by reacting an amino acid with a fatty acid halide, e.g. a chloride under basic conditions in aqueous conditions such as a water/THF solvent system. Yield and reaction times may be improved by applying heat to the reaction mixture. In an alternative embodiment, a fatty acid can be reacted with an amino acid in dioxane in the presence of DCC (dicyclohexylcarbodiimide) and 1-hydroxypyrrolidine-2,5-dione.

In yet another embodiment, an amino acid alkyl ester may be reacted with a fatty acid chloride under basic conditions in an aqueous-based solvent, such as a water/THF solvent system. Thereafter, the ester can be hydrolysed carefully without affecting the amide bond in basic methanol water solution In yet another embodiment, a fatty acid and an amino acid alkyl ester can be reacted in dioxane in the presence of DCC (dicyclohexylcarbodiimide) and 1-hydroxypyrrolidine-2,5-dione. The ester can be hydrolysed carefully without affecting the amide bond in dilute basic methanol water solution In yet another embodiment, a (mixed) anhydride of a fatty acid is reacted with an amino acid in dioxane.

In yet another embodiment, a fatty acid alkyl ester can be reacted with an amino acid in dioxane In still another embodiment, an amino acid alkyl ester is reacted with a triglyceride, optionally in the presence of a co-solvent. The amino acid ester thus formed is then hydrolysed according to a method described above.

In yet another embodiment, an amino acid is reacted with a triglyceride, optionally in the presence of a co-solvent.

In yet another embodiment, an amino acid is reacted with a triglyceride in the presence of a lipase, esterase, peptidase, amidase or acylase, optionally in the presence of a cosolvent and/or water.

In yet another embodiment a fatty acid alkyl ester is reacted with an amino acid in the presence of a lipase or an acylase, optionally in the presence of a co-solvent and/or water.

The compounds of formula (I) impart remarkable organoleptic properties to edible compositions to which they are added. In particular, they impart highly intense, authentic and harmonious flavour, and a roundness and fullness to edible compositions containing them.

More particularly, the compounds can be incorporated into an edible product to impart a remarkable mouthfeel, body and enhanced fat perception; or an enhanced umami or salt taste; or a cooling and richness. They are particularly useful in applications low in fat, salt and umami. They are also useful in fat-free formulations such as beverages and oral care applications. They also find use in dairy applications and in vanilla, cocoa and chocolate This finding was all the more surprising considering that when applicant tasted the compounds in dilute aqueous solution, they were either tasteless or they exhibited a disappointing, faintly fatty taste profile. As such, they appeared to be quite unsuitable for use in flavour applications. Only their combination with flavour co-ingredients and the judicious selection of their usage levels was it possible to discover the remarkable organoleptic properties of these compounds. Their effect on edible compositions is quite unusual in that rather than exerting a characteristic flavour profile to a foodstuff or a beverage, they actually complement, lift or accentuate the essential or authentic flavour and mouth feel characteristics of the foods or beverages in which they are incorporated. Accordingly, the compounds of the present invention find utility in a broad spectrum of applications in the food and beverage industry, as well as in health and wellness.

Accordingly, the invention provides in another of its aspects, a method of conferring flavour and/or mouthfeel to, or improving taste and/or mouthfeel of an edible composition, which method comprises adding to said composition a compound of formula (I) defined herein.

The remarkable organoleptic effects are observed when the compounds of formula (I) are incorporated into an edible composition containing one or more flavour co-ingredients.

The flavour co-ingredients may be sugars, fats, salt (e.g. sodium chloride), MSG, calcium ions, phosphate ions, organic acids, proteins, purines and mixtures thereof.

In a particular embodiment, sugars are present in amounts of 0.001% to 90%, more particularly 0.001% to 50%, still more particularly 0.001% to 20% based on the total weight of an edible composition.

In a particular embodiment, fats are present in amounts of 0.001% to 100%, more particularly 0.001% to 80%, more particularly 0.001% to 30%, still more particularly 0.001% to 5% based on the total weight of an edible composition.

In a particular embodiment, salt (e.g. sodium chloride) is present in amounts of 0.001% to 20%, more particularly 0.001% to 5% based on the total weight of an edible composition.

In a particular embodiment, MSG is present in amounts of 0.001% to 2% based on the total weight of an edible composition.

In a particular embodiment, calcium is present in amounts of 0.001% tot 50% more particularly 0.001% to 20%, still more particularly 0.001% to 1% based on the total weight of an edible composition.

In a particular embodiment, organic acids are present in amounts of 0.001% to 10%, more particularly 0.001% to 7% based on the total weight of an edible composition.

Types of organic acids include citric, malic, tartaric, fumaric, lactic, acetic, succinic. Types of edible compositions containing organic acids include beverages, such as carbonated soft drink beverages, still beverages, Juices, powdered soft drinks, liquid concentrates, alcoholic beverages and functional beverages.

In a particular embodiment, phosphorus is present in an amount up to 0.5% by weight of an edible composition. Typically phosphorus will be present as a phosphate or as phosphoric acid.

In a particular embodiment, purines are present in an amount up to 0.5% by weight of an edible composition. The term "purines" include ribonucleotides such as IMP and GMP.

Despite their interesting organoleptic properties, nevertheless, applicant found that formulating the compounds of formula (I) was not a trivial matter. The discovered potency of the compounds suggested that they could be employed at very low levels in flavour applications, and so for ease of handling, mixing and processing with other ingredients, although it is possible to use the compounds in neat form, it is desirable to extend or add volume to the physical form of the compounds by incorporating them into a suitable vehicle, for example a diluent, such as a solvent. However, the compounds are solids or viscous oils at ambient temperatures, and have very limited solubility in water. Applicant found that an at least about 0.01% stock solution, more particularly about 0.01-1% stock solution of a compound of formula (I) achieved a balance regarding acceptable solvent levels for ease of handling and mixing, and the desire to limit the amount of solvent that would have to be removed from the stock solution when further processing of the compounds in flavour compositions and edible products for reasons of palatability, efficiency, cost and the like. Applicant found that suitable solvents for the stock solution include ethanol, triacetine, glycerol and miglyol.

In order to aid in the process of solubilization and produce a stock solution and minimize the amount of solvent, it is preferred to use compounds of the formula (I) formed from a mixture of carboxylic acids, rather than a pure carboxylic acid.

Accordingly, the invention provides in another of its aspects an at least about 0.01% stock solution, more particularly about 0.01-1% stock solution of a compound of formula (I).

The stock solution may contain other materials such as carrier materials and/or adjuvants more fully described below. In a particular embodiment, the stock solution contains an anti-oxidant selected from the group consisting of vitamin C, vitamin E, rosemary extract, antrancine, butylated hydroxyanisole (BHA) and butylated hydroxytoluene (BHT). Anti-oxidants are preferably employed to prevent, or significantly reduce, generation of volatile off notes as a result of degradation of the compounds of formula (I). Anti-oxidants are particularly preferred when the compounds of formula (I) bear a residue of an unsaturated fatty acid. Anti-oxidants are particularly preferred if the fatty acid residue contains more than 1 double bond. Determination of an effective amount of anti-oxidant is within the purview of the skilled person, however amounts in the range of about 10 ppm to 1000 ppm based on the weight of the stock solution may be present.

In preparing the flavour compositions of the present invention, the compounds of formula (I) may be employed in any physical form. They may be used in neat form, in the form of a stock solution described above; they may be used in the form of an emulsion; or they may be used in a powder form. If the compounds of formula (I) are presented in the form of a powder, the powder form can be produced by a dispersive evaporation process, such as a spray drying process as is more fully described below. The powder form may be prepared by subjecting a liquid formulation containing a compound of formula (I) to a dispersive evaporation process. The liquid formulation may comprise a solution, suspension or emulsion comprising the compound of formula (I). In particular, the liquid formulation may take the form of the stock solution described hereinabove. The liquid formulation may contain other ingredients such as a carrier material and/or an adjuvant as described more fully below.

A powder comprising a compound of formula (I) forms another aspect of the present invention.

The compounds of formula (I) may in incorporated into an edible composition alone, or in the form of a flavour composition comprising one or more flavour co-ingredients.

A flavour composition comprising a compound according to the formula (I) forms another aspect of the present invention.

In an embodiment of the present invention, the flavour formulation comprises a compound of formula (I) and at least flavour co-ingredient.

In a particular embodiment of the present invention the flavour composition comprises:
  i) a compound according to formula (I);
  ii) at least one flavour co-ingredient;
  iii) optionally a carrier material; and
  iv) optionally at least one adjuvant.

By the term "flavour co-ingredient" is an ingredient that is able to contribute or impart or modify in a positive or pleasant way the taste of an edible composition.

All manner of flavour co-ingredients may be employed in a composition according to the present invention, including, but not limited to natural flavours, artificial flavours, spices, seasonings, and the like. Flavour co-ingredients include synthetic flavour oils and flavouring aromatics and/or oils, oleoresins, essences, distillates, and extracts derived from plants, leaves, flowers, fruits, and so forth, and combinations comprising at least one of the foregoing.

Flavour oils include spearmint oil, cinnamon oil, oil of wintergreen (methyl salicylate), peppermint oil, Japanese mint oil, clove oil, bay oil, anise oil, eucalyptus oil, thyme oil, cedar leaf oil, oil of nutmeg, allspice, oil of sage, mace, oil of bitter almonds, and cassia oil; useful flavouring agents include artificial, natural and synthetic fruit flavours such as vanilla, and citrus oils including lemon, orange, lime, grapefruit, yazu, sudachi, and fruit essences including apple, pear, peach, grape, blueberry, strawberry, raspberry, cherry, plum, prune, raisin, cola, guarana, neroli, pineapple, apricot, banana, melon, apricot, ume, cherry, raspberry, blackberry, tropical fruit, mango, mangosteen, pomegranate, papaya and the like.

Additional exemplary flavours imparted by a flavouring agent include a milk flavour, a butter flavour, a cheese flavour, a cream flavour, and a yogurt flavour; a vanilla flavour; tea or coffee flavours, such as a green tea flavour, an oolong tea flavour, a tea flavour, a cocoa flavour, a chocolate flavour, and a coffee flavour; mint flavours, such as a peppermint flavour, a spearmint flavour, and a Japanese mint flavour; spicy flavours, such as an asafetida flavour, an ajowan flavour, an anise flavour, an angelica flavour, a fennel flavour, an allspice flavour, a cinnamon flavour, a chamomile flavour, a mustard flavour, a cardamom flavour, a caraway flavour, a cumin flavour, a clove flavour, a pepper flavour, a coriander flavour, a sassafras flavour, a savoury flavour, a Zanthoxyli Fructus flavour, a perilla flavour, a juniper berry flavour, a ginger flavour, a star anise flavour, a horseradish flavour, a thyme flavour, a tarragon flavour, a dill flavour, a capsicum flavour, a nutmeg flavour, a basil flavour, a marjoram flavour, a rosemary flavour, a bayleaf flavour, and a wasabi (Japanese horseradish) flavour; a nut flavour such as an almond flavour, a hazelnut flavour, a macadamia nut flavour, a peanut flavour, a pecan flavour, a pistachio flavour, and a walnut flavour; alcoholic flavours, such as a wine flavour, a whisky flavour, a brandy flavour, a rum flavour, a gin flavour, and a liqueur flavour; floral flavours; and vegetable flavours, such as an onion flavour, a garlic flavour, a cabbage flavour, a carrot flavour, a celery flavour, mushroom flavour, and a tomato flavour.

In some embodiments, said flavour co-ingredients include aldehydes and esters such as cinnamyl acetate, cinnamaldehyde, citral diethylacetal, dihydrocarvyl acetate, eugenyl formate, p-methylamisol, and so forth can be used. Further examples of aldehyde flavourings include acetaldehyde (apple), benzaldehyde (cherry, almond), anisic aldehyde (licorice, anise), cinnamic aldehyde (cinnamon), citral, i.e., alpha-citral (lemon, lime), neral, i.e., beta-citral (lemon, lime), decanal (orange, lemon), ethyl vanillin (vanilla, cream), heliotrope, i.e., piperonal (vanilla, cream), vanillin (vanilla, cream), alpha-amyl cinnamaldehyde (spicy fruity flavours), butyraldehyde (butter, cheese), valeraldehyde (butter, cheese), citronellal (modifies, many types), decanal (citrus fruits), aldehyde C-8 (citrus fruits), aldehyde C-9 (citrus fruits), aldehyde C-12 (citrus fruits), 2-ethyl butyraldehyde (berry fruits), hexenal, i.e., trans-2 (berry fruits), tolyl aldehyde (cherry, almond), veratraldehyde (vanilla), 2,6-dimethyl-5-heptenal, i.e., melonal (melon), 2,6-dimethyloctanal (green fruit), and 2-dodecenal (citrus, mandarin), and the like.

Further examples of other flavour co-ingredients can be found in "Chemicals Used in Food Processing", publication 1274, pages 63-258, by the National Academy of Sciences.

Flavour co-ingredients can also include salt tastants, umami tastants, and savoury flavour compounds. Non limiting examples include: NaCl, KCl, MSG, guanosine monophosphate (GMP), inosin monophospahte (IMP), ribonucleotides such as disodium inosinate, disodium guanylate, N-(2-hydroxyethyl)-lactamide, N-lactoyl-GMP, N-lactoyl tyramine, gamma amino butyric acid, allyl cysteine, 1-(2-hydroxy-4-methoxylphenyl)-3-(pyridine-2-yl)propan-1-one, arginine, potassium chloride, ammonium chloride, succinic acid, N-(2-methoxy-4-methyl benzyl)-N'-(2-(pyridin-2-yl)ethyl) oxalamide, N-(heptan-4-yl)benzo(D)(1,3)dioxole-5-carboxamide, N-(2,4-dimethoxybenzyl)-N'-(2-(pyridin-2-yl)ethyl) oxalamide, N-(2-methoxy-4-methyl benzyl)-N'-2(2-(5-methyl pyridin-2-yl)ethyl) oxalamide, cyclopropyl-E,Z-2,6-nonadienamide.

In particular embodiments of the present invention, the flavour co-ingredient is selected from the compounds and compositions disclosed in WO2005102701, WO2006009425, WO2005096843, WO2006046853 and WO2005096844, all of which references are herein incorporated by reference in their entirety.

Flavour co-ingredients may include known salt tastants, umami tastants, and savoury flavour compounds. Non limiting examples include: NaCl, KCl, MSG, guanosine monophosphate (GMP), inosin monophospahte (IMP), ribonucleotides such as disodium inosinate, disodium guanylate, N-(2-hydroxyethyl)-lactamide, N-lactoyl-GMP, N-lactoyl tyramine, gamma amino butyric acid, allyl cysteine, 1-(2-hydroxy-4-methoxylphenyl)-3-(pyridine-2-yl)propan-1-one, arginine, potassium chloride, ammonium chloride, succinic acid, N-(2-methoxy-4-methyl benzyl)-N'-(2-(pyridin-2-yl)ethyl) oxalamide, N-(heptan-4-yl)benzo(D)(1,3)dioxole-5-carboxamide, N-(2,4-dimethoxybenzyl)-N'-(2-(pyridin-2-yl)ethyl) oxalamide, N-(2-methoxy-4-methyl benzyl)-N'-2(2-(5-methyl pyridin-2-yl)ethyl) oxalamide, cyclopropyl-E,Z-2,6-nonadienamide.

The carrier material may be employed in compositions according to the invention to encapsulate or to entrap in a matrix the other components of the composition. The role of the carrier material may be merely that of a processing aid or a bulking agent, or it might be employed to shield or protect the other components from the effects of moisture or oxygen or any other aggressive media. The carrier material might also act as a means of controlling the release of flavour from edible compositions.

Carrier materials may include mono, di- or trisaccharides, natural or modified starches, hydrocolloids, cellulose derivatives, polyvinyl acetates, polyvinylalcohols, proteins or pectins. Example of particular carrier materials include sucrose, glucose, lactose, levulose, fructose, maltose, ribose, dextrose, isomalt, sorbitol, mannitol, xylitol, lactitol, maltitol, pentatol, arabinose, pentose, xylose, galactose, maltodextrin, dextrin, chemically modified starch, hydrogenated starch hydrolysate, succinylated or hydrolysed starch, agar, carrageenan, gum arabic, gum accacia, tragacanth, alginates, methyl cellulose, carboxymethyl cellulose, hydroxyethyl cellulose, hydroxypropylmethyl cellulose, derivatives and mixtures thereof. Of course, the skilled addressed with appreciate that the cited materials are hereby given by way of example and are not to be interpreted as limiting the invention.

By "flavour adjuvant" is meant an ingredient capable of imparting additional added benefit to compositions of the present invention such as a colour, light resistance, chemical stability and the like. Suitable adjuvants include solvents (including water, alcohol, ethanol, triacetine, oils, fats, vegetable oil and miglyol), binders, diluents, disintegrating agents, lubricants, colouring agents, preservatives, antioxidants, emulsifiers, stabilisers, anti-caking agents, and the like. In a particular embodiment, the flavour composition comprises an anti-oxidant. Said anti-oxidants may include vitamin C, vitamin E, rosemary extract, antrancine, butylated hydroxyanisole (BHA) and butylated hydroxytoluene (BHT).

Examples of such carriers or adjuvants for flavour compositions may be found in for example, "Perfume and Flavour Materials of Natural Origin", S. Arctander, Ed., Elizabeth, N.J., 1960; in "Perfume and Flavour Chemicals", S. Arctander, Ed., Vol. I & II, Allured Publishing Corporation, Carol Stream, USA, 1994; in "Flavourings", E. Ziegler and H. Ziegler (ed.), Wiley-VCH Weinheim, 1998, and "CTFA Cosmetic Ingredient Handbook", J. M. Nikitakis (ed.), 1st ed., The Cosmetic, Toiletry and Fragrance Association, Inc., Washington, 1988.

Other suitable and desirable ingredients of flavour compositions are described in standard texts, such as "Handbook of Industrial Chemical Additives", ed. M. and I. Ash, $2^{nd}$ Ed., (Synapse 2000).

Flavour compositions according to the present invention may be provided in any suitable physical form. For example, they may be in the form of oils, emulsions or dispersions in a hydrous liquid or organic liquid suitable for use in edible compositions, or solid form, such as powders.

If the flavour compositions are to be provided in the form of a powdered composition, they may be prepared by dispersive evaporation techniques generally known in the art, such as spray drying.

Accordingly, in another aspect of the present invention there is provided a method of forming a powder composition, comprising the steps of providing a liquid composition comprising a compound of the formula (I) and one or more optional ingredients selected from at least one flavour co-ingredient, a carrier material and an adjuvant, and dispersively evaporating said liquid composition to form a powder composition.

In this manner, a compound of formula (I) or a flavour composition comprising said compound may be presented in a powder form.

The liquid composition used in the preparation of a powder may be in the form of a solution, emulsion, dispersion or slurry. The liquid may contain water, and/or an organic liquid, such as ethanol, glycerol, triacetine, miglyol (MCT) that is acceptable for use in edible compositions.

Powder compositions according to the present invention may be prepared according to methods and apparatus known in the art for producing powders on an industrial scale. A particularly suitable method is spray drying. Spray drying techniques and apparatus are well known in the art and need no detailed discussion herein. The spray drying techniques, apparatus and methods described in US2005/0031769 and US2013/0022728, as well as those techniques, apparatus and methods described in those documents are suitable for producing powder compositions of the present invention and are herein incorporated by reference in their entirety.

The manner in which the compounds of formula (I) are incorporated into powder flavour compositions of the invention is not critical. For example, the compounds may be added to the liquid composition described above and be subjected to a dispersive evaporation process along with all the other components of the flavour composition. Alternatively, compounds may be added to the flavour composition after it has been formed as a powder.

Many of the flavour co-ingredients described herein above are volatile and/or may be sensitive to oxidative degradation, particularly when subjected to elevated temperature, and under humid conditions. Accordingly, particular problems can arise when subjecting flavour co-ingredients described above to dispersive evaporation processes such as spray drying. A non-exhaustive list of ingredients that can be particularly susceptible include, those ingredients containing artificial, natural or synthetic fruit flavours such as vanilla, chocolate, coffee, cocoa and citrus oil, including lemon, orange, grape, lime and grapefruit, and fruit essences including apple, pear, peach, strawberry, raspberry, cherry, plum, pineapple, apricot and the like. The volatile components of these flavour co-ingredients may include, but are not limited to, acetaldehyde, dimethyl sulfide, ethyl acetate, ethyl propionate, methyl butyrate, and ethyl butyrate. Flavour co-ingredients containing volatile aldehydes or esters include, e.g., cinnamyl acetate, cinnamaldehyde, citral, diethylacetal, dihydrocarvyl acetate, eugenyl formate, and p-methylanisole. Further examples of volatile compounds that may be present as co-ingredients include acetaldehyde (apple); benzaldehyde (cherry, almond); cinnamic aldehyde (cinnamon); citral, i.e., alpha citral (lemon, lime); neral, i.e., beta citral (lemon, lime); decanal (orange, lemon); ethyl vanillin (vanilla, cream); heliotropine, i.e., piperonal (vanilla, cream); vanillin (vanilla, cream); alpha-amyl cinnamaldehyde (spicy fruity flavors); butyraldehyde (butter, cheese); valeraldehyde (butter, cheese); citronellal (modifies, many types); decanal (citrus fruits); aldehyde C-8 (citrus fruits); aldehyde C-9 (citrus fruits); aldehyde C-12 (citrus fruits); 2-ethyl butyraldehyde (berry fruits); hexenal, i.e., trans-2 (berry fruits); tolyl aldehyde (cherry, almond); veratraldehyde (vanilla); 2,6-dimethyl-5-heptenal, i.e., melonal (melon); 2-6-dimethyloctanal (green fruit); and 2-dodecenal (citrus, mandarin); cherry; or grape and mixtures thereof.

Applicant surprisingly found that the inclusion of a compound of formula (I) in a powder flavour composition, it was possible to maintain the flavour quality of flavour composition converted into powdered form by a dispersive evaporation process.

Accordingly, the invention provides in another of its aspects a method of maintaining flavour quality of a powder flavour composition comprising the step of including in said powder flavour composition a compound of formula (I)

As stated hereinabove, compounds of formula (I) or flavour compositions containing such compounds can be incorporated into edible compostions, and an edible composition containing such a compound or flavour composition forms another aspect of the present invention.

The term "edible composition" refers to products for consumption by a subject, typically via the oral cavity (although consumption may occur via non-oral means such as inhalation), for at least one of the purposes of enjoyment, nourishment, or health and wellness benefits. Edible compositions may be present in any form including, but not limited to, liquids, solids, semi-solids, tablets, capsules, lozenges, strips, powders, gels, gums, pastes, slurries, syrups, aerosols and sprays. The term also refers to, for example, dietary and nutritional supplements. Edible compositions include compositions that are placed within the oral cavity for a period of time before being discarded but not swallowed. It may be placed in the mouth before being consumed, or it may be held in the mouth for a period of time before being discarded. An edible composition as herein above defined includes compositions whose taste is modified in the manner described herein by the addition of compounds of formula (I) or whose taste is so modified by processing such that it is enriched in a compound of formula (I).

In a particular embodiment the term "edible compositions" refers to products for consumption by a subject, typically via the oral cavity (although consumption may occur via non-oral means such as inhalation), for one of the purposes of enjoyment or nourishment.

In a more particular embodiment the term "edible compositions" refers to products for consumption by a subject, typically via the oral cavity (although consumption may occur via non-oral means such as inhalation), for the purpose of enjoyment. Still more particularly, the term refers to foodstuffs and beverages.

In a particular embodiment, the term "edible composition" does not relate to pharmaceutical compositions.

In another embodiment, the term "edible composition" does not relate to nutritional supplements.

Broadly, the edible composition includes, but is not limited to foodstuffs of all kinds, confectionery products, baked products, sweet products, savoury products, fermented products, dairy products, beverages and oral care products.

Exemplary foodstuffs include, but are not limited to, chilled snacks, sweet and savoury snacks, fruit snacks, chips/crisps, extruded snacks, tortilla/corn chips, popcorn, pretzels, nuts, other sweet and savoury snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, uht soup, frozen soup, pasta, canned pasta, dried pasta, chilled/fresh pasta, noodles, plain noodles, instant noodles, cups/bowl instant noodles, pouch instant noodles, chilled noodles, snack noodles, dried food, dessert mixes, sauces, dressings and condiments, herbs and spices, spreads, jams and preserves, honey, chocolate spreads, nut-based spreads, and yeast-based spreads.

Exemplary confectionery products include, but are not limited to, chewing gum (which includes sugarized gum, sugar-free gum, functional gum and bubble gum), centerfill confections, chocolate and other chocolate confectionery, medicated confectionery, lozenges, tablets, pastilles, mints, standard mints, power mints, chewy candies, hard candies, boiled candies, breath and other oral care films or strips, candy canes, lollipops, gummies, jellies, fudge, caramel, hard and soft panned goods, toffee, taffy, liquorice, gelatin candies, gum drops, jelly beans, nougats, fondants, combinations of one or more of the above, and edible flavour compositions incorporating one or more of the above.

Exemplary baked products include, but are not limited to, alfajores, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savoury biscuits and crackers, bread substitutes, Exemplary sweet products include, but are not limited to, breakfast cereals, ready-to-eat ("rte") cereals, family breakfast cereals, flakes, muesli, other ready to eat cereals, children's breakfast cereals, hot cereals, Exemplary savoury products include, but are not limited to, salty snacks (potato chips, crisps, nuts, tortilla-tostada, pretzels, cheese snacks, corn snacks, potato-snacks, ready-to-eat popcorn, microwaveable popcorn, pork rinds, nuts, crackers, cracker snacks, breakfast cereals, meats, aspic, cured meats (ham, bacon), luncheon/breakfast meats (hot-dogs, cold cuts, sausage), tomato products, margarine, peanut butter, soup (clear, canned, cream, instant, UHT), canned vegetables, pasta sauces.

Exemplary dairy products include, but are not limited to, cheese, cheese sauces, cheese-based products, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, dairy products, milk, fresh/pasteurized milk, full fat fresh/pasteurized milk, semi skimmed fresh/pasteurized milk, long-life/uht milk, full fat long life/uht milk, semi skimmed long life/uht milk, fat-free long life/uht milk, goat milk, condensed/evaporated milk, plain condensed/evaporated milk, flavoured, functional and other condensed milk, flavoured milk drinks, dairy only flavoured milk drinks, flavoured milk drinks with fruit juice, soy milk, sour milk drinks, fermented dairy drinks, coffee whiteners, powder milk, flavoured powder milk drinks, cream, yoghurt, plain/natural yoghurt, flavoured yoghurt, fruited yoghurt, probiotic yoghurt, drinking yoghurt, regular drinking yoghurt, probiotic drinking yoghurt, chilled and shelf-stable desserts, dairy-based desserts, soy-based desserts.

Exemplary beverages include, but are not limited to, flavoured water, soft drinks, fruit drinks, coffee-based drinks, tea-based drinks, juice-based drinks (includes fruit and vegetable), milk-based drinks, gel drinks, carbonated or non-carbonated drinks, powdered drinks, alcoholic or non-alcoholic drinks.

Exemplary fermented foods include, but are not limited to, Cheese and cheese products, meat and meat products, soy and soy products, fish and fish products, grain and grain products, fruit and fruit products.

In a particular embodiment the consumable product is selected from the group consisting of soy sauce, cheese, soup, hot and cold sauces, fruits, vegetables, ketchups, tea, coffee, snacks such as potato chips or extruded snacks.

The compounds of formula (I), when added to a flavour composition and/or an edible composition act on the composition to complement its flavour and/or mouthfeel to render it more delicious and authentic. The effects may be temporal or related to intensity, for example the compounds may act by enhancing, strengthening, softening, sharpening a flavour, or making more salivating. The compounds of formula (I) may also affect the temporal profile of a flavour, that is, they may affect the initial impact of a flavour, the body of a flavour, or its lingering effect.

The compounds of formula (I) may modify any aspect of the temporal profile of taste or flavour of an edible composition. In particular, the compounds improve mouthfeel and impart more creamy and fatty sensations.

Compounds of formula (I) or flavour compositions containing same may be added to edible compositions in widely carrying amounts. The amount will depend on the nature of the edible composition to be flavoured, and on the desired effect, as well as on the nature of the ingredients present in said flavour composition. In order to obtain the remarkable beneficial effects attributed to the presence of the compounds of formula (I), the flavour composition should be employed in amounts such that the compounds of formula (I) are present in amounts of 1 part per billion to 10 parts per million based on the total weight of the edible composition. Whereas amounts higher than this can be employed, the beneficial effects are considerably less apparent and undesirable off-notes can become increasingly apparent.

Interesting organoleptic effects, e.g. salt, alcohol or coolant boosting effects, in edible compositions containing salt or alcohol or coolant compounds can be achieved when compounds of the formula (I) are employed at levels of 1 to 100 ppb.

Interesting organoleptic effects, for example umami boosting effects, in edible compositions containing umami tastants can be achieved when compounds of the formula (I) are employed at levels of 100 to 250 ppb.

Interesting organoleptic effects, in particular mouthfeel boosting effects, in edible compositions can be achieved when compounds of the formula (I) are employed at levels of 250 to 500 ppb.

Interesting organoleptic effects, e.g. fat boosting effects, in edible compositions containing fats can be achieved when compounds of the formula (I) are employed at levels of 500 to 1000 ppb.

It is particularly advantageous to incorporate compounds of formula (I) into edible compositions that are formed under conditions of high temperature, such as baking, frying or which are processed by heat treatments such as pasteurization or under UHT conditions. Under high preparation or processing temperatures, volatile flavour ingredients may be lost or degraded with the result that flavour intensity can be reduced and the essential and authentic flavour characteristics can be diminished. Such edible products include dairy products, snack foods, baked products, powdered soft drinks and similar dry mixes, and the like, fats and condiments, mayonnaise, dressings, soups and bouillons, and beverages.

A particularly preferred class of edible composition according to the present invention are powdered soft drinks and similar dry mix applications. Dry mix applications are known in the art and included products in powder form that are intended to be reconstituted before consumption. They include powdered soups, powdered cake mixes, powdered chocolate drinks, instant coffees, seasonings and fonds, and the like.

Dry powders formed by dispersive evaporation processes, such as spray drying, represent a very convenient vehicle to deliver flavour oil quality flavours to edible compositions.

Unfortunately, flavour oils, and in particular citrus flavour oils can be particularly sensitive to dispersive evaporation processes, especially processes carried out at high temperature. Flavour oils tend to evaporate or degrade to form products having unfavourable off-notes. Powdered flavour compositions, particularly those containing citrus oils, can be of poor quality and exhibit relatively short self-life, as a result.

Surprisingly, the incorporation of compounds of formula (I) or flavour compositions containing same into powder compositions, results in powder compositions that exhibit the impact and authenticity of the flavour oils used in their preparation, essentially maintaining flavour oil quality in a powdered flavour formulations.

Accordingly, the invention provides in another aspect a powder flavour composition comprising a compound according to formula (I) and at least one additional flavour co-ingredient.

In another aspect of the invention there is provided a powder soft drink composition or other dry mix composition comprising a compound according to formula (I).

In yet another aspect of the present invention there is provided a powder soft drink composition or other dry mix composition comprising a powder flavour composition comprising a compound of formula (I).

In yet another aspect of the present invention there is provided a method of forming a powder flavour composition comprising the step of incorporating into said composition a compound according to formula (I).

In a particular embodiment of the compound of formula (I) may be added to the formed powder flavour composition, or it may be added to flavour composition before forming the powder.

Another particularly preferred class of edible composition according to the present invention are snack foods. Snack foods are a category of product well known to the skilled person in the food industry. These products are described above and include, without limitation, pretzels, corn chips, potato chips, puffed products, extruded products, tortilla chips and the like. Still more particularly, the invention is concerned with low fat snack food compositions. Low fat snack food compositions contain less that 30% by weight fat, more particularly between 5 to 25% by weight of fat.

A problem with reducing fat in a snack food composition is the loss in taste and texture. Fats play an important role in the way that dough behaves during processing and greatly affect the quality, flavor and texture of ready-to-eat products. As the fat content in snack products is reduced or replaced with other ingredients (e.g., non-digestible fat, protein, fiber, gums), adverse organoleptic effects (e.g., mouth coating, drying, lack of crispness and lack of flavour) are increased. The adverse organoleptic effects result in products having reduced palatability.

Considerable efforts have been expended in devising flavour compositions to overcome the problems associated with low fat snack food products. Flavours may be applied to a snack food as topical coatings in the form of dry powders and/or as liquids (e.g., oil-based, water-based). Another approach has been to add flavour to the dough.

Despite these various approaches which have been taken to improve consumer appeal and palatability of snack foods, and particularly low fat snack foods, there is still a need for improved low-fat snack foods having coatings applied thereto with the visual appeal, flavor, and texture of full-fat snack foods.

Compounds according to formula (I) or flavour compositions containing same can be incorporated into snack foods to impart an impactful flavour and a mouthfeel with a remarkable roundness and fullness. Furthermore, the taste and mouthfeel effects can be achieved even in low fat snack foods.

Accordingly, the invention provides in another of its aspects a snack food comprising a flavour composition as hereinabove described. In a particular embodiment of the invention the snack food has a fat content of about 40% or less by weight based on the total weight of the snack food, more particularly about 30% or less, still more particularly 25% or less, more particularly still about 10% or less, still more particularly about 5% or less, still more particularly about 3% or less.

Examples of snack foods are described above and include products processed by oven baking, extrusion or frying, and which are made from potato and/or corn and/or various grains such as rice or wheat.

Another particularly preferred class of edible composition according to the present invention is alcoholic beverages.

Applicant surprisingly found that compounds according to formula (I) incorporated into an alcoholic beverage had the effect of increasing the alcohol impact of the beverage.

Accordingly, the invention provides in another of its aspects an alcoholic beverage comprising a compound according to formula (I).

In yet another aspect of the invention there is provided a method of producing a heightened alcoholic impression in an alcoholic beverage by incorporating into said beverage a compound according to formula (I).

Compounds of formula (I) may be incorporated into said alcoholic beverage in amounts of 1 ppb to 1 ppm.

Another preferred class of edible compositions are products ingested in the form of tablets, capsules, powders, multiparticulates and the like.

Certain groups of people have problems swallowing tablets or capsules, powders, multiparticulates and the like. This problem can be particularly pronounced in certain consumer groups, such as children and the very old or infirm. Applicant surprisingly found that compounds according to the formula (I) when taken into the oral cavity produce a pronounced salivating effect. Incorporating the compounds into these dosage forms, particularly as part of a coating around said dosage forms can ease the swallowing process for consumers, in particular children and the old or infirm.

Accordingly, the invention provides in another of its aspects an orally administrable dosage form, in particular in the form of tablets capsules, powders or multiparticulates comprising a compound according to the formula (I).

Another preferred class of edible composition is baked goods. Compounds of the formula (I) may be incorporated topically or in-dough. Incorporated at levels of 1 ppb to 1 ppm, the compounds of formula (I) render baked products less dry and more succulent.

Other preferred class of edible compositions are caloric or non-caloric beverages containing carbohydrate sweeteners, such as sucrose, high fructose corn syrup, fructose and glucose, or high intensity, non-nutritive sweeteners such as aspartame, acesulfame K, sucralose, cyclamate, sodium saccharin, neotame, rebaudioside A, and/or other stevia-based sweeteners; as well as other optional ingredients such as juices, organic acids such as citric acid, alcohol and functional ingredients.

Incorporated at levels of 1 ppb to 10 ppm, compounds of formula (I) impart to said beverages containing sweeteners at levels of less than 1% and up to about 20%, an upfront sweetness and mouthfeel that is reminiscent of sugar.

Other preferred edible compositions are savoury compositions, in particular those that are soy-based or fish-based.

Incorporated at levels of 1 ppb to 10 ppm, in a soy-based composition (such as soy sauce) or a fish-based composition (such as fish sauce) containing 5 to 40% salt, the compositions are found to exhibit strong umami tastes that are long-lasting and rich.

Another preferred edible composition is a clouded beverage composition.

Certain beverages such as juices have relatively higher turbidity and thus have an opaque appearance. Often, it is desired that the beverage have a relatively high turbidity. This might be desirable to provide a more natural appearance to beverages with low juice content, or it might be for reasons related to masking sedimentation or "ringing" (where flavour or colour oils rise to the surface of a container during storage). Clouded beverages are usually formed by means of a clouding agent. Clouding agents are usually supplied in the form of emulsions, or the clouding agent may be part of a powdered beverage that upon reconstitution will formed an emulsion providing a permanent cloud to the beverage.

Compounds of the formula (I), in addition to their remarkable organoleptic properties, can lend stability to clouding agents and to beverage compositions containing same.

Accordingly, the invention provides in another of its aspects a composition comprising a beverage clouding composition and a compound of formula (I).

In a particular embodiment of the invention, a flavour composition as herein defined may be provided in the form of an emulsion. This emulsion composition may be particularly useful in clouded beverage applications, in particular, in which it is intended to employ a clouding agent.

In yet another aspect of the invention there is provided a clouded beverage composition comprising a clouding agent and a compound of the formula (I).

Other preferred edible compositions are those compositions that are formed by a process of ripening.

In food processing, it frequently occurs that a food needs to remain for a prolonged period of time and under well-defined conditions to obtain the food with the requisite and recognised quality. A commonly used term for this process is ripening. Ripening is well known in the processing of certain types of cheese, meat, soy-sauce and wine, as well as beer sausage, sauerkraut, tempeh and tofu. There are also specific steps that are carried out for specific reasons (such as water-removal, or off-note removal) that have beneficial effects on the food products. Examples of this are the conching of chocolate and the drying of noodles, vegetables and fruits. The transformations that improve the quality of the food are induced by chemical conversions, enzymatically catalysed conversions or fermentative transformations. All of these conversions are slow and therefore expensive; they are also not fully predictable or controllable.

The compounds of formula (I), having regard to their remarkable property of adding to the authentic taste characteristics of the edible compositions in which they are incorporated, may be added to an edible product during its ripening process in order to reduce storage time without adversely influencing the taste quality of the ripened product.

Accordingly, in another aspect of the invention there is provided a method of ripening a product selected from the group consisting of cheese, meat, soy-sauce and wine, beer, sausage, sauerkraut, tempeh and tofu, comprising the step of ripening the product in the presence of a compound according to the formula (I).

In another aspect of the invention there is provided a method of conching chocolate, said method comprising the step of adding to the chocolate a compound according to the formula (I), or a flavour composition containing same.

There now follows a series of non-limiting examples that serve to illustrate the invention.

SYNTHESIS EXAMPLES

1. General Structure

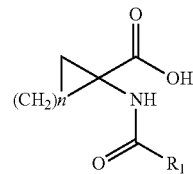

$R_1$ is a straight chain hydrocarbon group having 9 to 21 carbon atoms and containing zero to three double bonds
or
$R_1$ is a [(1E)-2,6-dimethylhepta-1,5-dien-1-yl]-group
and n=1 to 4

Several compounds belonging to that general formula have been synthesised according to one of the 2 procedure described below.

2. Synthesis 2.1 Route A: (DCC method)

In a 250 mL round-bottomed flask was mixed fatty acid (3.93 mmol) with 1-hydroxypyrrolidine-2,5-dione (0.498 g, 4.32 mmol) in dioxane (50 ml) to give a colorless solution. The solution was cooled to 10° C. and DCC (0.892 g, 4.32 mmol) was added while stirring. Stirring was continued for three hours at room temperature. The formed solids were filtered (dicyclohexylurea) and the filtrate was added to a solution of amino acid (6.48 mmol) in a 2% solution of sodiumbicarbonate (0.363 g, 4.32 mmol) in water. The reaction mixture was stirred for 4 hours at 50° C. Dioxane was evaporated and the aqueous residue was further diluted with water, acidified with a diluted hydrochloric acid solution and extracted with ethylacetate. Organic layers were combined, washed with brine, dried and evaporated to yield 1.3 g of a white solid. Product was purified by flash column chromatography, eluent DCM/methanol.

1 g of 85-90% pure product could be obtained.

2.2 Route B (DCC method with protection group)

Step 1:

To a solution of an O-methylated amino acid (16.51 mmol) in DCM (100 ml) was added triethylamine (1.519 g, 15.01 mmol) at minus 15° C. A fatty acid (0.01 mmol) was added while stirring. A solution of DCC (15.01 mmol) in 10 mL of DCM was added dropwise at 0° C. The reaction mixture was stirred at 0° C. for 1 hour and stirring was continued at room temperature for 3 hours. The dicyclohexylurea was removed by filtration from the reaction mixture. Filtrate was washed with a saturated sodiumbicarbonate solution, diluted hydrochloric acid solution and water. Organic layer was separated, dried and evaporated to yield 3 g of an oil. This oil was purified by flash column chromatography, eluent DCM/methanol The intermediate ester compound could be isolated in a purity of 95%.

Step 2:

The O-methylated N-acyl-amino-acid (4.91 mmol) was dissolved in a mixture of Ethanol (8.00 ml) and water (8 ml). To this mixture was added a 32% solution of sodiumhydroxide (2.453 g, 19.63 mmol) and mixture was stirred at room temperature for three hours. Mixture stand over for 14 hours.

After 14 hours the mixture was acidified with a concentrated hydrochloric acid solution (1.612 ml, 19.63 mmol), diluted with water and extracted with mtbe. Organic layer was separated, dried and evaporated. 1.3 g of a half solid yellow residue was obtained. NMR confirmed the structure of the title compound, purity 95%

2.3 Route C (acid chloride)

An amino acid (20 mmol) was dissolved in a solution of sodiumhydroxide (54.5 mmol) in water (40 ml).

Tetrahydrofuran (60 ml) was added. Fatty acid chloride (18.18 mmol) was added dropwise at room temperature. Stirring was continued for 2 hours. Mixture was diluted with water, acidified with a 37% solution of hydrochloric acid (2.99 ml, 36.4 mmol) and extracted with ethylacetate.

Organic layers were combined, dried and evaporated.

The residue contains about 20% free fatty acid according NMR. The solids were stirred with heptane for 30 minutes, filtered and dried. This resulted in 2.4 g of the title compound as a creamy colored solid. (purity 95%).

2.4 All synthesized products Based on the above described methods a series of compounds have been synthesized. All these compounds are summarized in table 1.

ACC=1-Amino-cyclopropane carboxylic acid

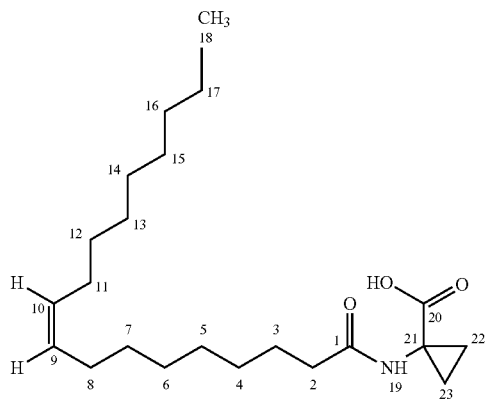

TABLE 1

List of synthesized compounds

| Structure | Amino acid | Carboxylic acid | Structure | Route |
|---|---|---|---|---|
| 1 | ACC | C10:0 | | C |
| 2 | ACC | C10:2 | | A |
| 3 | ACC | C16:0 | | C |
| 4 | ACC | C18:0 | | C |
| 5 | ACC | C18:1 | | C |
| 6 | ACC | C18:2 | | A |

3 NMR data (example)
3.1 Structure 5, ACC-C18:1

$^1$H NMR (600 MHz, CHLOROFORM-d) δ ppm 0.88 (t, J=7.05 Hz, 3 H, H—C (18)) 1.09-1.21 (m, 2H H—C (22, 23)) 1.21-1.1.39 (m, 20 H, H—C (4, 5, 6, 7, 12, 13, 14, 15, 16, 17)) 1.54-1.68 (m, 4 H, H—C (3, 22, 23)) 1.91-2.07 (m, 4H, H—C (8, 11)) 2.18 (t, J=7.73 Hz, 2 H, H—C (2)) 5.26-5.44 (m, 2 H, H—C (9, 10)) 6.28 (s, 1 H, H—N (19))

$^{13}$C NMR (150 MHz, CHLOROFORM-d) δ ppm 14.13 (C (18) 18.01 (C (22, 23)) 22.69 (C (17)), 25.45 (C (3)), 27.19 (C (11) 27.23 (C11)) 29.16 (C4)) 29.18 (C6)) 29.26 (C (5)) 29.33 (C (13, 15)) 29.45 (C (14)) 29.72 (C (7)) 29.78 (C (12)) 31.91 (C (16, 21)) 33.47 (C (2)) 129.76 (C (10)) 129.99 (C (9)) 175.15 (C (1)) 177.39 (C (20))

APPLICATION EXAMPLES

Testing of C18 amino cyclopropanic acid (ACCA) derivative

Samples were prepared and evaluated by expert tasters. Tasters were asked to describe the samples focusing on authentic taste, mouthfeel, fullness, salivation, salty-ness, umami, sweetness, juiciness, richness, long lastingness and fattiness.

Test on Kikkoman soy sauce low salt
  Salt level pure product between 5-40%
  Salt level in application 0.3-1.0%
  C18:1-ACCA: 0.5 ppm Strong upfront saltiness lingering, very strong saltiness Test in fish sauce
  Salt level pure product between 5-40%
  Salt level in application 0.3-1.0%
  C18:1-ACCA 0.5 ppm, —Strong saltiness lingering, strong body mouthfeel Test in mayonnaise
  Fat levels between 10-80%
  Low fat Mayonnaise (27% Fat)
  C18:1-ACCA 0.5 ppm—Nice balanced, full mouthfeel, increased eggyness Test in dressings
  Oil levels 0.5-50%
  Acidity PH 3-6
  Low fat salad dressing (13.6% Fat)
  C18:1-ACCA 0.5 ppm—Increased mouthfeel body less acidic Test in Soups and Bouillons
  Fat levels 0.1-10%
  Salt levels 0.3-1.4%
  Standard Chicken bouillon base
  0.7% salt, 0.5% fat
  C18:1-ACCA 0.5 ppm—More body and fatty notes, salivating and good aftertaste
  C18:1-ACCA 0.2 ppm—Saltier, Stronger and more umami Test in Jus and Fonds
Beef jus
  C18:1-ACCA 40 ppb—more salty, fatty, total profile is enhanced Test in Cheese
  Fat level: 1-40%
  Salt: 0.3-2%
Spreadable cheese ERU
  C18:1-ACCA 0.5 ppm—Strong umami, lingering cheese bite
Cheese sauce: 5% fat 1.6% salt
  C18:1-ACCA 0.5 ppm—Strong umami, cheese bite, expanding

The invention claimed is:

1. A flavor composition adapted for use in an edible composition comprising:
  1 ppb to 10 ppm by weight based upon the weight of the edible composition of a compound selected from the group consisting of:
    N-palmitoyl 1-amino-cyclopropyl carboxylic acid (C16:0-ACCA),
    N-stearoyl 1-amino-cyclopropyl carboxylic acid (C18:0-ACCA),
    N-linoleoyl 1-amino-cyclopropyl carboxylic acid (C18:2-ACCA),
    N-linolenoyl 1-amino-cyclopropyl carboxylic acid (C18:2-ACCA),
    N-oleoyl 1-amino-cyclopropyl carboxylic acid (C18:1-ACCA),
    N-(9-palmitenoyi) 1-amino-cyclopropyl carboxylic acid (C16:1-ACCA),
    N-decanoyl 1-amino-cyclopropyl carboxylic acid (C10:0-ACCA), and,
    N-geranoyl 1-amino-cyclopropyl carboxylic acid (C10:2-ACCA),
  wherein,
  one or more of the foregoing compounds accentuates the existing flavour or existing mouth feel characteristics of an edible foodstuff product which further comprises at least one flavour co-ingredient, or of a beverage product which further comprises at least one flavour co-ingredient, when one or more of the foregoing compounds are incorporated therein.

2. A stock solution comprising 0.01 to 1% by weight of a compound selected from the group consisting of:
    N-palmitoyl 1-amino-cyclopropyl carboxylic acid (C16:0-ACCA),
    N-stearoyl 1-amino-cyclopropyl carboxylic acid (C18:0-ACCA),
    N-linoleoyl 1-amino-cyclopropyl carboxylic acid (C18:2-ACCA),
    N-linolenoyl 1-amino-cyclopropyl carboxylic acid (C18:2-ACCA),
    N-oleoyl 1-amino-cyclopropyl carboxylic acid (C18:1-ACCA),
    N-(9-palmitenoyl) 1-amino-cyclopropyl carboxylic acid (C16:1-ACCA),
    N-decanoyl 1-amino-cyclopropyl carboxylic acid (C10:0-ACCA), and,
    N-geranoyl 1-amino-cyclopropyl carboxylic acid (C10:2-ACCA),
  wherein,
  one or more of the foregoing compounds accentuates the existing flavour or existing mouth feel characteristics of an edible foodstuff product which further comprises at least one flavour co-ingredient, or of a beverage product which further comprises at least one flavour co-ingredient, when one or more of the foregoing compounds are incorporated therein at concentrations of 1 ppb to 10 ppm by weight based on the weight of the edible foodstuff product or beverage product.

3. A stock solution according to claim 2 which further comprises a solvent selected from the group consisting of: ethanol, triacetine, glycerol and miglyol and mixtures thereof.

4. A flavour composition according to claim 1 further comprising an ingredient selected from the group consisting of: sugars, fats, salt, MSG, calcium ions, phosphate ions, organic acids, proteins, purines and mixtures thereof.

5. A flavour composition according to claim 1 further comprising a carrier material and an adjuvant.

6. A flavour composition according to claim 5 wherein the adjuvant is an anti-oxidant.

7. A flavour composition according to claim 1 wherein the flavour composition is in the form of an emulsion.

8. A flavour composition according to claim 1 wherein the flavour composition is in the form of a powder.

9. A flavour composition according to claim 8 wherein the flavour composition is a spray dried powder.

10. A flavour composition adapted for use in an edible composition according to claim 1, which flavor composition is in the form of a powdered soft drink or a dry mix composition.

11. A flavour composition adapted for use in an edible composition according to claim 1 in the form of a snack food wherein the flavor composition is incorporated in the snack food or is applied topically to the snack food as a powder.

12. A flavour composition according to claim 1 in an alcoholic beverage.

13. A flavour composition according to claim 1 in an orally administrable tablet, capsule, powder or multiparticulate.

14. A flavour composition according to claim 1 in a caloric or non-caloric beverage further containing at least one carbohydrate sweetener selected from: sucrose, high fructose corn syrup, fructose and glucose, or at least one high intensity, non-nutritive sweetener selected from: aspartame, acesulfame K, sucralose, cyclamate, sodium saccharin, neotame, rebaudioside A, and/or stevia-based sweeteners.

15. A flavour composition according to claim 1 in a soy-based edible composition.

16. A flavor composition according to claim 1, wherein the compound provides an organoleptic, fat booting effect flavor when included in an edible foodstuff product or beverage product.

17. A flavor composition according to claim 1, wherein the compound provides an organoleptic, alcohol boosting effect flavor when included in an edible foodstuff product or beverage product.

18. A flavor composition according to claim 1, wherein the compound provides an organoleptic, coolant boosting effect flavor when included in an edible foodstuff product or beverage product.

19. A flavor composition according to claim 1, wherein the compound provides an organoleptic, umami boosting effect flavor when included in an edible foodstuff product or beverage product.

20. A flavor composition according to claim 1, wherein the compound imparts sweetness and mouthfeel reminiscent of sugar when present in a beverage product.

21. A flavor composition according to claim 1, wherein the compound imparts stability in a clouded beverage composition.

22. A flavor composition according to claim 1 in the form of an emulsion.

* * * * *